United States Patent
Kim

(10) Patent No.: US 11,324,636 B2
(45) Date of Patent: May 10, 2022

(54) AUTOMATIC CERUMEN REMOVING DEVICE

(71) Applicant: OROLOGYLAB HEALTHCARE INC., Gyeonggi-Do (KR)

(72) Inventor: Young-Tae Kim, Gyeonggi-do (KR)

(73) Assignee: OROLOGYLAB HEALTHCARE INC., Gyeonggi-Do (KR)

( * ) Notice: Subject to any disclaimer, the term of this patent is extended or adjusted under 35 U.S.C. 154(b) by 133 days.

(21) Appl. No.: 16/739,185

(22) Filed: Jan. 10, 2020

(65) Prior Publication Data

US 2020/0214894 A1 Jul. 9, 2020

Related U.S. Application Data

(63) Continuation of application No. PCT/KR2019/000185, filed on Jan. 7, 2019.

(51) Int. Cl.
*A61F 11/00* (2022.01)
*A61B 17/00* (2006.01)

(52) U.S. Cl.
CPC ... *A61F 11/006* (2013.01); *A61B 2017/00398* (2013.01)

(58) Field of Classification Search
CPC ........ A61B 2017/00398; A61F 11/006; A61M 3/0258; A61M 3/0287; A61M 2210/0062
See application file for complete search history.

(56) References Cited

U.S. PATENT DOCUMENTS

| | | | |
|---|---|---|---|
| 5,203,037 A | 4/1993 | Kang | |
| 5,860,968 A * | 1/1999 | Wojcik | A61B 18/22 606/10 |
| 6,187,021 B1 * | 2/2001 | Wim | A61F 11/006 606/161 |
| 9,788,693 B1 * | 10/2017 | Zhou | A46B 13/02 |
| 2006/0041197 A1 * | 2/2006 | Ophardt | G07F 9/02 600/437 |
| 2007/0009368 A1 | 1/2007 | Yang | |
| 2008/0183125 A1 * | 7/2008 | Issa | A61F 11/006 604/26 |
| 2011/0015489 A1 * | 1/2011 | Raghuprasad | A61B 1/227 600/187 |
| 2016/0135995 A1 | 5/2016 | Burres | |

(Continued)

FOREIGN PATENT DOCUMENTS

| | | |
|---|---|---|
| DE | 202006008072 U1 | 9/2006 |
| EP | 0937422 A2 | 8/1999 |
| JP | 4304646 B2 | 7/2009 |

(Continued)

OTHER PUBLICATIONS

Internatinal Search Report of PCT/KR2018/000185, dated Oct. 4, 2019.

(Continued)

*Primary Examiner* — Jocelin C Tanner
(74) *Attorney, Agent, or Firm* — W&KIP

(57) ABSTRACT

The present application provides a cerumen removing device, comprising a container section comprising a recovery hole and a discharge hole; a head section exposed to the outside through the recovery hole and having at least one air ejection hole; and a pump configured to discharge air to the outside through the air ejection hole.

15 Claims, 5 Drawing Sheets

(56) References Cited

U.S. PATENT DOCUMENTS

2017/0143946 A1* 5/2017 Martin .................... A61F 11/00

FOREIGN PATENT DOCUMENTS

| KR | 1992-0006770 U | 9/1992 |
| KR | 20-0265705 Y1 | 2/2002 |
| KR | 20030093657 A | 12/2003 |
| KR | 20-2010-0006110 U | 6/2010 |
| KR | 10-2010-0086286 A | 7/2010 |
| KR | 10-2011-0087690 A | 8/2011 |

OTHER PUBLICATIONS

Writen Opinion of PCT/KR2018/000185, dated Oct. 4, 2019.
Office Action From Korean PTO of KR10-2018-0093687, dated Jan. 17, 2020.
Ross J Roeser. J Am Acad Audiol 8:391-400 (1997).
Extended European Search Report for European Application No. 19829392.0.

* cited by examiner

AUTOMATIC CERUMEN REMOVING DEVICE

CROSS-REFERENCE TO RELATED APPLICATIONS

This application is a continuation application of International Patent Application No. PCT/KR2019/000185 with an international filing date of Jan. 7, 2019, designating the United States, now pending. The contents of all of the aforementioned application is incorporated herein by reference.

TECHNICAL FIELD

The present application relates to an automatic cerumen removing device, and relates to an automatic cerumen removing device capable of automatically, safely and effectively removing dry cerumen, oily cerumen and animal cerumen.

BACKGROUND

Cerumen physiologically plays an important role in suppressing the invasion of bacteria from the outside through an ear canal, thereby minimizing infection of the ear.

Even if the cerumen is not removed artificially, it will easily fall off the ear inner skin due to skin movement within the ear (ear canal) caused by natural movement of the temporomandibular joint and surrounding muscles when people talk or chew food, and the cerumen can be gradually pushed out of the ear with continuous movement of the skin. Therefore, it is not medically recommended to remove cerumen artificially.

Because, when removing cerumen, the removing tool is inserted deep into the ear to remove cerumen, and it is even possible that the minimum required amount of cerumen is removed. When a removing tool such as a cotton swab which has one end with a size to block the entire ear hole is used, the removing tool pushes the cerumen deep into the ear, which leads to an increased risk of side effects.

However, despite the above medical understanding and recommendation, removing cerumen is still a matter of personal choice related to personal hygiene. In particular, the actual situation is different from the medical instructions, and the cerumen will stay in the ear for a long time without artificial removal, as a result, the cerumen will cause a feeling of clogging, foreign body sensation and even skin irritation during movement of the cerumen. Therefore, when a certain amount of cerumen accumulates in the ear, the desire to remove the cerumen is usually very strong.

For the above reasons, people in most cultural circles in the world have habits of removing cerumen for a long time, and nowadays, most people in the world regularly remove cerumen in their daily lives.

In spite of the general demand for removing cerumen, when using earpicks and cotton swabs or similar cerumen removing tools in traditional way for removing cerumen on the world market, users cannot directly see their ears and still rely on their feeling to remove the cerumen, therefore, the users are hindered from removing their own cerumen by themselves effectively and safely. In addition, the elderly and children who have relatively poor delicate force adjustment ability may apply too much force on the surface of the skin in the ear due to operation error of the tool, which may cause skin wounds or inflammation and even more if the tool is inserted too deep into the ear, it may also cause injury or perforation of the eardrum.

In order to solve the problem that the user can't see the inside of his/her own ear, a cerumen removing tool with a built-in USB-type mini camera is recently developed. However, as the user is able to see the cerumen, it will increase the motivation to completely remove the cerumen, which may have the shortcoming of inducing a psychological demand of removing the cerumen excessively. In addition, because the removing of the cerumen is in a manual way, the safety of the operation cannot be ensured, and the safety problem for being used by the elderly and children is still unsolved.

In addition, automatically removing the cerumen through a vacuum suction method improves the condition of inconvenience caused by removing cerumen manually, and at the same time, the cerumen remover with a safety design that can prevent the end of the cerumen remover from being inserted deep into the ear in the vacuum suction method needs to have sufficient vacuum suction force, which requires to increase the suction vacuum pressure sufficiently or reduce the area of the suction inlet sufficiently. However, increasing the vacuum pressure increases the potential risk of injuring the eardrum, therefore, only a minimum pressure level can be used, and the suction force can only be increased relatively by reducing the area of the suction inlet. Therefore, when the suction inlet is not precisely aligned with the position of the cerumen inside the ear, there is a disadvantage that the cerumen removal efficiency is very low because of the low suction pressure.

In addition, the tip of the traditional earpick has a diameter of several millimeters and has a spoon-like shape, and the earpick has a structure that is adapted for easily removing dry and oily cerumen. A handle section connected to the tip is designed to have a very thin structure with a thickness of several millimeters adapted for easy insertion into the ear. The traditional earpick is mainly made of hard materials such as metal, wood, and plastics such that the tip of the tool can contact the skin surface in the ear and apply sufficient force to the skin surface.

However, the tip structure and material may apply considerable pressure on the skin surface, and a contact portion between the tip structure and the skin surface is mainly the edge portion of the spoon-like structure. At this time, the force applied to the contact portion is equivalent to the gravity generated by several hundred grams to several kilograms, therefore a high pressure level of tens of MPa will be instantaneously applied to the skin surface.

Therefore, when the force applied to the surface is not finely controlled, severe pain is caused and at the same time inflammation is caused by skin damage. In addition, as the inside of the ear can't be directly viewed, the cerumen is generally removed according to one's feeling. Even if other people help to remove the cerumen, the field of vision is still limited, such that the cerumen can only be removed according to one's feeling or only the cerumen on the visible outer part of the ear canal can be removed. In particular, people with poor skin conditions who are very sensitive to external stimuli, or the elderly or children who are more sensitive to external stimuli, will feel intense irritation, therefore there is a need to develop a very comfortable cerumen removing tool.

On the one hand, unlike Asians, in the West, 92.4% of white people (caucasian) and 96.9% of black people (negroid) and 98% of the European population have waxy oily cerumen (wet earwax), and about 50% of the elderly of 65 years old has symptoms of cerumen impaction that the cerumen completely block the ear canal for every few months (J. Am Acad Audiol 1997 (86) 391-400).

Ears with the symptoms of cerumen impaction mostly produce a feeling of severe blockage. Reports from the Otorhinolaryngology Department show that the above symptom will lead to about 20 dB of hearing loss, which will cause great communication problems and become a major obstacle to the daily life of the elderly. In this situation, the cerumen needs to be removed regularly in the hospital, which results in considerable economic losses. In order to prevent cerumen impaction symptoms in elderly people, it is necessary to develop a technology for an intelligent cerumen removing device that monitors the number of cerumen removals performed by users within a predetermined period and can perform personal hygiene management of cerumen removal.

In addition, unlike humans, pets such as dogs and cats are recommended to regularly have their cerumen removed. Pet cerumen is removed roughly with a cotton swab-shaped machine tool and a cerumen dissolving solvent in liquid form. Humans are also recommended to have the cerumen removed with liquid cerumen dissolving agent, however, this method is also inconvenient to be used, therefore the cotton swab-shaped mechanical tool is often used to remove the cerumen. However, when using an inserted swab-shaped tool, there is a side effect of pushing the cerumen further into the ear, and it is difficult for the user to insert the tool to a safe depth according to the feeling and sensation thereof. Therefore, it is necessary to develop a cerumen removing tool capable of setting a safe depth according to the size of a pet, which has safety, convenience, and can make the pet feel comfortable.

SUMMARY

Technical Problem

An objective of the present application is to provide an automatic cerumen removing device capable of automatically removing cerumen in order to solve the above-mentioned problems.

Technical Means to Solve the Problems

In order to achieve the above objective, according to an embodiment of the present application, a cerumen removing device is provided, which comprises: a container section comprising a recovery hole and a discharge hole; a head section exposed to the outside through the recovery hole and having at least one air ejection hole; and a pump configured to discharge air to the outside through the air ejection hole.

In addition, the air ejection hole is formed to direct the discharged air towards the recovery hole, and when the recovery hole contacts an ear of an user, flowing of the air discharged by the air ejection hole on an inner wall of an ear canal of the user is enhanced and the air sequentially pass through the recovery hole and the discharge hole.

Furthermore, the air ejection hole forms an angle of 45° to 90° with an assumed central axis using the central axis as a base line.

Additionally, the head section comprises a flow path member having a predetermined length and having an air passage connected to the air ejection hole.

Still further, the head section is configured to be curved toward a wall surface of an ear canal so that at least part of the head section is in contact with the wall surface of the ear canal.

Furthermore, the head section comprises a scrub head which has the air ejection hole and is in contact with a wall surface of an ear canal.

In addition, the cerumen removing device comprises a motor for rotating the head section.

Still further, the motor is a stepping motor.

In addition, the cerumen removing device comprises a driving part for moving the head section forward or backward.

Additionally, the driving part comprises a linear guide.

Furthermore, the cerumen removing device comprises an operation part which is connected to the head section and exposed to the outside for moving the head section forward or backward.

In addition, the cerumen removing device comprises a user identification section configured to store and identify device usage information of a user.

Additionally, a cerumen removing device is provided, and the head section thereof is configured to move with a unit sector angle of 5° to 20° on a wall surface of an ear canal.

Furthermore, a cerumen removing device is provided, and the head section thereof is configured to scrub a wall surface of an ear canal at a scrubbing speed of 5 mm/s to 50 mm/s.

Still further, a cerumen removing device is provided, and a circular contact surface disposed on the head section thereof for scrubbing a wall surface of an ear canal has a width of 0.5 mm to 2 mm.

Additionally, a cerumen removing device is provided, and a circular contact surface disposed on the head section thereof for scrubbing a wall surface of an ear canal is provided with a micro-pattern.

Effects of the Present Application

According to the present application, the problem of directly applying pressure to the eardrum can be fundamentally prevented by discharging the air towards the outside of the ear canal (towards the recovery hole). Therefore, the cerumen removing device has an effect to prevent discomfort felt by the user due to air pressure applied to the eardrum.

In addition, as described above, by discharging the air, the cerumen removing device has an effect to remove and evaporate moisture, which is introduced into the ear of the user during face washing or bathing, to the outside of the ear.

In addition, according to the present application, the scrubbing and the air ejection operations are performed simultaneously by the head section of the cerumen removing device, therefore, the removal efficiency of both dry cerumen and oily cerumen can be improved.

In addition, according to the present application, the driving part can work in an automatic mode or a manual mode according to the state of the user, such as the age of the user, thereby enabling easier use.

In addition, according to the present application, various information of the user can be stored in the device and on the Internet, therefore, the information can be communicated to an application program, and the effects including the following can be realized: being able to confirm the stored use information of the user, the application program analyzing the information of the user, and providing appropriate warnings and suggestions in voice and text form.

DETAILED DESCRIPTION

Figure 1:
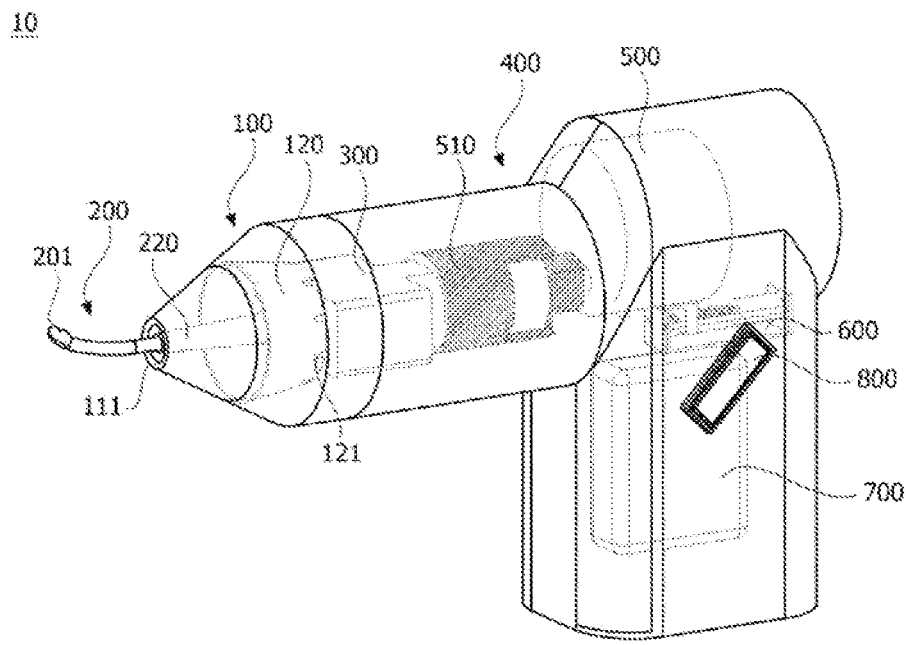
FIG. 1 is an internal perspective view of a cerumen removing device according to an embodiment of the present application.

Hereinafter, preferred embodiments of the present application will be described in detail with reference to the drawings. Previously, the terms or words used in this specification and the claims should not be limited to ordinary or lexicographical meanings, and should be interpreted as meanings and concepts consistent with the technical idea of the present application based on the principle that the inventors appropriately define the concept of terms in order to explain their applications in the best manner.

In addition, irrespective of the reference numerals, the same or corresponding constituent elements are marked with the same or similar reference numerals, and repeated descriptions of the reference numerals are omitted. For convenience of explanation, the size and shape of each constituent member may be enlarged or reduced.

Therefore, the embodiments and illustrated structures described in the specification are only the most preferred embodiments of the present application and cannot represent all the technical ideas of the present application. Therefore, it should be understood that the present application may comprise various equivalents and variants as alternatives of the above embodiments.

The present application relates to an automatic cerumen removing device 10. According to an exemplary automatic cerumen removing device of the present application, the present application relates to an automatic cerumen removing device capable of automatically, safely, and efficiently removing cerumen of various shapes.

Figure 2:
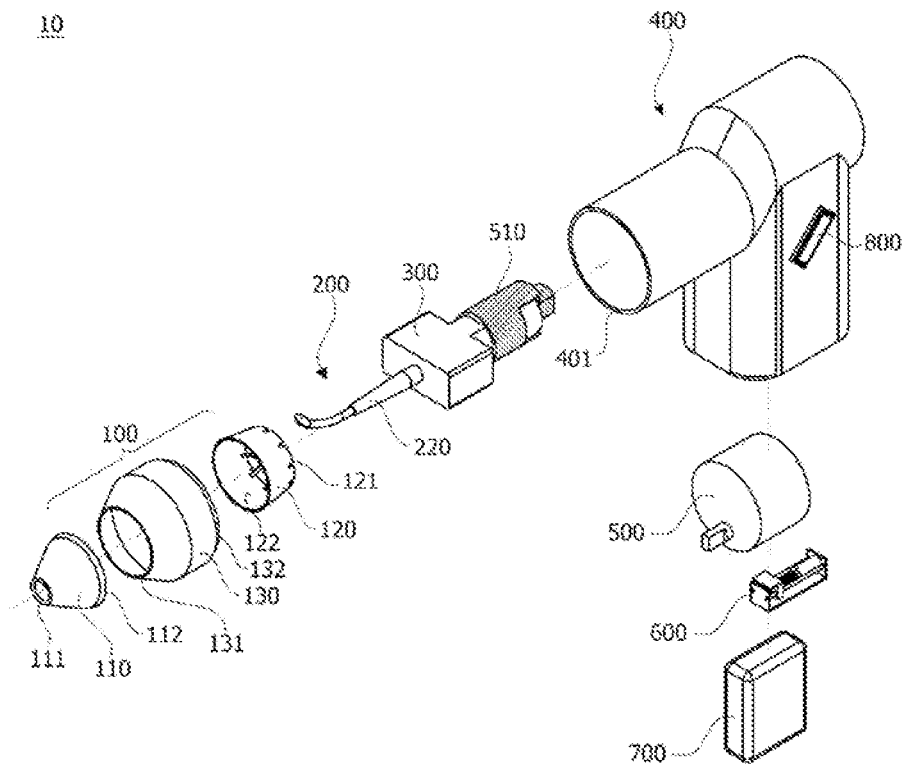
FIG. 2 is an exploded perspective view of a cerumen removing device according to an embodiment of the present application.

FIG. 1 is an internal perspective view of an automatic cerumen removing device 10 according to an embodiment of the present application, and FIG. 2 is an exploded perspective view of the automatic cerumen removing device 10 according to an embodiment of the present application.

Referring to FIG. 1 and FIG. 2, the automatic cerumen removing device 10 according to an embodiment of the present application comprises a container section 100, a head section 200, and a pump 300.

The container section 100 may comprise a recovery hole 111 and a discharge hole 121.

In addition, the head section 200 is exposed to the outside through the recovery hole 111 and is provided with at least one air ejection hole 201.

In addition, the pump 300 can supply air so that the air flows through the air ejection hole 201 to the outside.

The pump 300 may be an air pump or an air fan.

More specifically, the cerumen removing device 10 according to an embodiment of the present application may comprise a body section 400 connected and installed to the container section 100.

The main body 400 may comprise an opening 401 provided on one side and a predetermined space connected to the opening 401.

In addition, the container section 100 may comprise a contact member 110 comprising a recovery hole 111 that is in contact with and supported by a user's ear hole, and a cerumen storage member 120 comprising a discharge hole 121.

Moreover, the container section 100 may further comprise a first connection member 130 for connecting the contact member 110 and the body section 400.

More specifically, the contact member 110 may comprise a recovery hole 111 and a mounting hole 112 formed in a direction opposite to the recovery hole 111.

The contact member 110 may be formed to have a hollow interior, and may have a cross-sectional area increasing from the recovery hole 111 toward the mounting hole 112 in an oblique arrangement.

For example, the contact member 110 may have a conical shape, but is not limited thereto.

In particular, the recovery hole 111 can be inserted into an ear hole, and is in close contact with the inner wall surface of the ear hole. For example, the contact relationship like that of an earphone inserted into the ear can be achieved.

The contact member 110 is made of a rubber material, and the rubber material may comprise, for example, ordinary rubber, synthetic rubber, soft rubber, and the like, but is not limited thereto.

Therefore, the contact member 110 made of a rubber material and comprising the recovery hole 111 that is in direct contact with the ear hole of the user has an effect of being in closer contact with the user's ear.

As described above, the cerumen removed from the wall surface of the ear canal is not discharged to the outside, but can be more easily introduced into the device by using the recovery hole 111 that is in close contact with the ear hole.

Also, the cerumen storage member 120 may comprise: a discharge hole 121 provided for discharging air; and an opening portion 122 having one open end.

Figure 3:
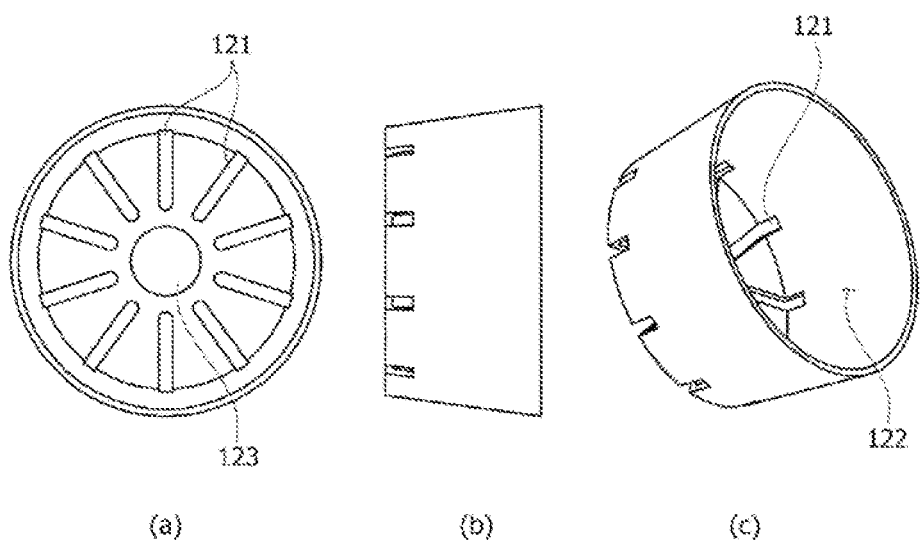
FIG. 3 is a perspective view of a cerumen storage member according to an embodiment of the present application.

FIG. 3 is a perspective view of a cerumen storage member 120 according to an embodiment of the present application.

Referring to FIG. 3, as an embodiment, the cerumen storage member 120 may comprise an opening portion 122 with one end open, and a discharge hole 121 formed in a direction opposite to the opening portion.

A plurality of the discharge holes 121 may be formed, and mesh member (not shown) with mesh structure may be further formed on the plurality of discharge holes 121.

As described above, the mesh member is disposed on the discharge hole to prevent the cerumen from being discharged to the outside.

For example, the discharge hole 121 may have a slit shape, but it is not limited to this, as long as the discharge hole 121 has a structure through which the air can pass, it can be used.

Figure 4:
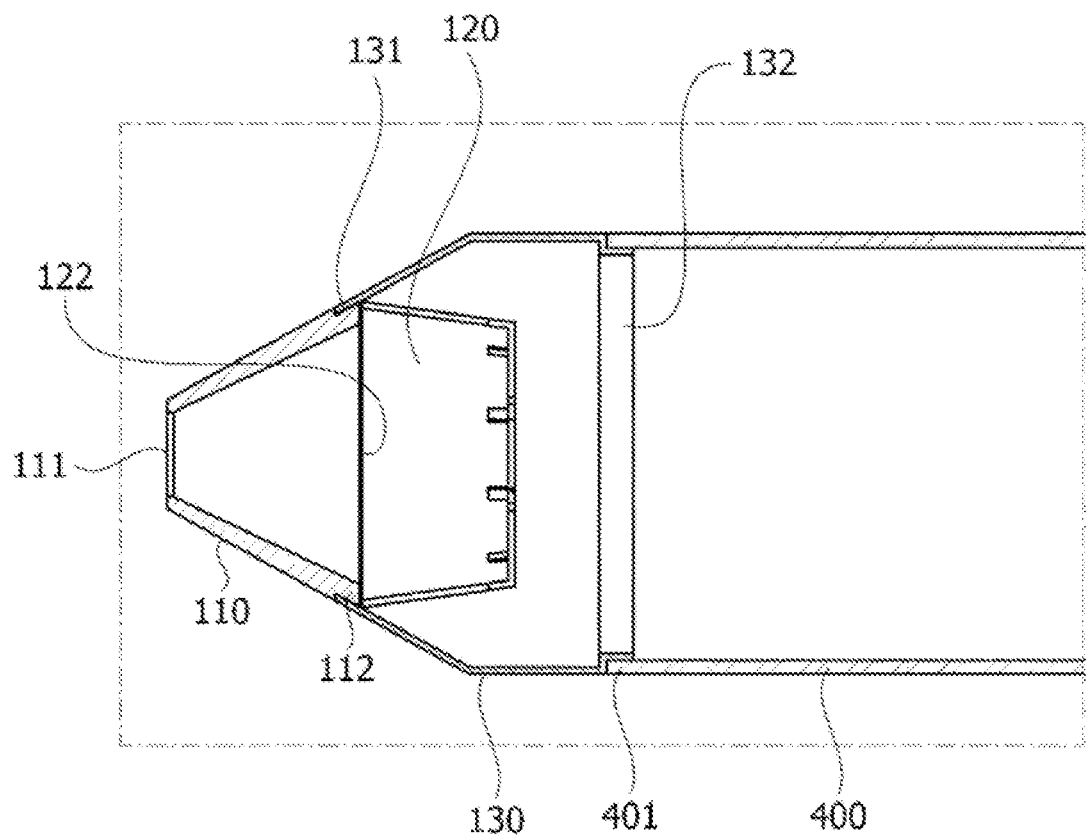
FIG. 4 is a partial sectional view of a cerumen removing device according to an embodiment of the present application.

FIG. 4 is a partial sectional view of a cerumen removing device 10 according to an embodiment of the present application.

Referring to FIG. 4, the opening portion 122 may be connected and installed to the mounting hole 112 of the contact member 110 so that the cerumen removed from the inner wall surface of the ear canal of the user can be received into the cerumen storage member 120 through the recovery hole 111.

At this time, the air introduced together with the cerumen can be discharged through the discharge hole 121.

Therefore, the mounting hole 112 may be formed corresponding to the opening portion 122 of the cerumen storage member 120.

In addition, an insertion hole 123 may be formed in a central region of the cerumen storage member 120.

The insertion hole 123 can be mounted onto a second connection member 220 described later by insertion, so that the cerumen storage member 120 can be fixed by the second connection member 220.

In addition, the plurality of discharge holes 121 may be provided at predetermined intervals along the circumferential direction of the insertion hole 123, but is not limited thereto.

Further, the first connection member 130 may be configured to receive the cerumen storage member 120 therein, and may comprise a first connection hole 131 connected to the mounting hole 112 and a second connection hole 132 connected to the opening 401.

Figure 5:
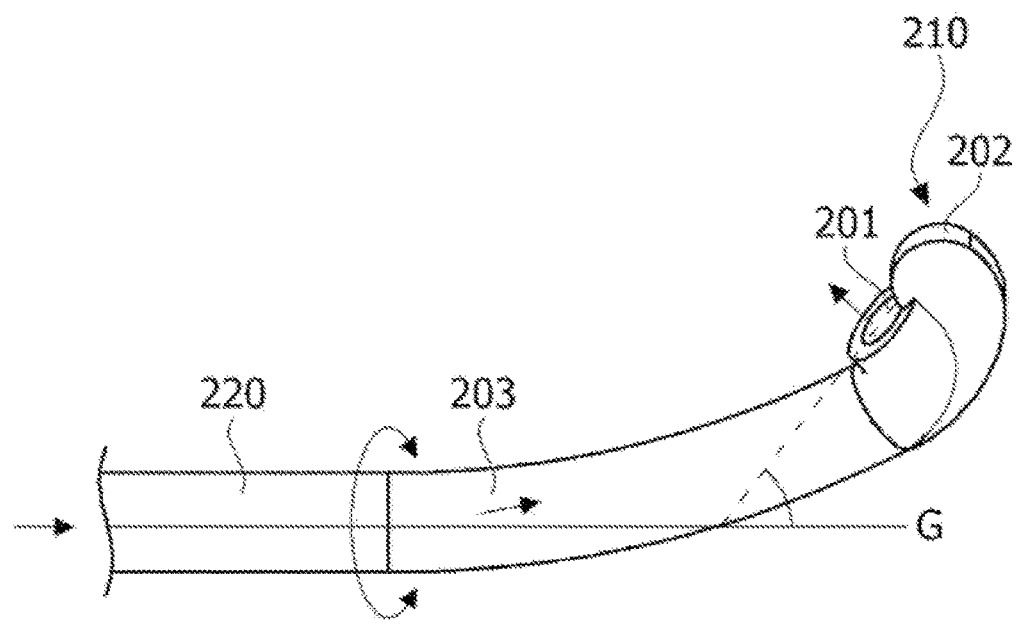
FIG. 5 is a schematic structure view showing a head section according to an embodiment of the present application.

In one aspect, FIG. 5 is a perspective view showing a head section 200 according to an embodiment of the present application.

Referring to FIG. 5, the head section 200 comprises a scrub head 210 which is provided with an air ejection hole 201 and is in contact with the wall surface of the ear canal.

The scrub head 210 contacts and scrubs the wall surface of the ear canal through a circular contact surface 202 provided circularly at the end of the head section 200, so that the user's cerumen can be removed from the ear canal wall.

Further, the head section 200 comprises a flow path member 203 having a predetermined length and having an air passage connected to the air ejection hole 201.

The flow path member 203 may be formed to have a predetermined length so that the scrub head 210 can be inserted into the ear canal at a predetermined depth to be able to remove the cerumen.

One side of the flow path member 203 is connected to the pump 300 in a way that a fluid can flow therethrough, so that the air supplied from the pump 300 passes through the air passage of the flow path member 203 and can be ejected to the inside of the ear canal through the air ejection hole 201.

The head section 200 may further comprise a second connection member 220 for connecting the pump 300 and the flow path member 203.

The second connection member 220 has a predetermined length and may form a flow channel inside so that air supplied from the pump 300 flows to the flow path member 203.

Figure 6:
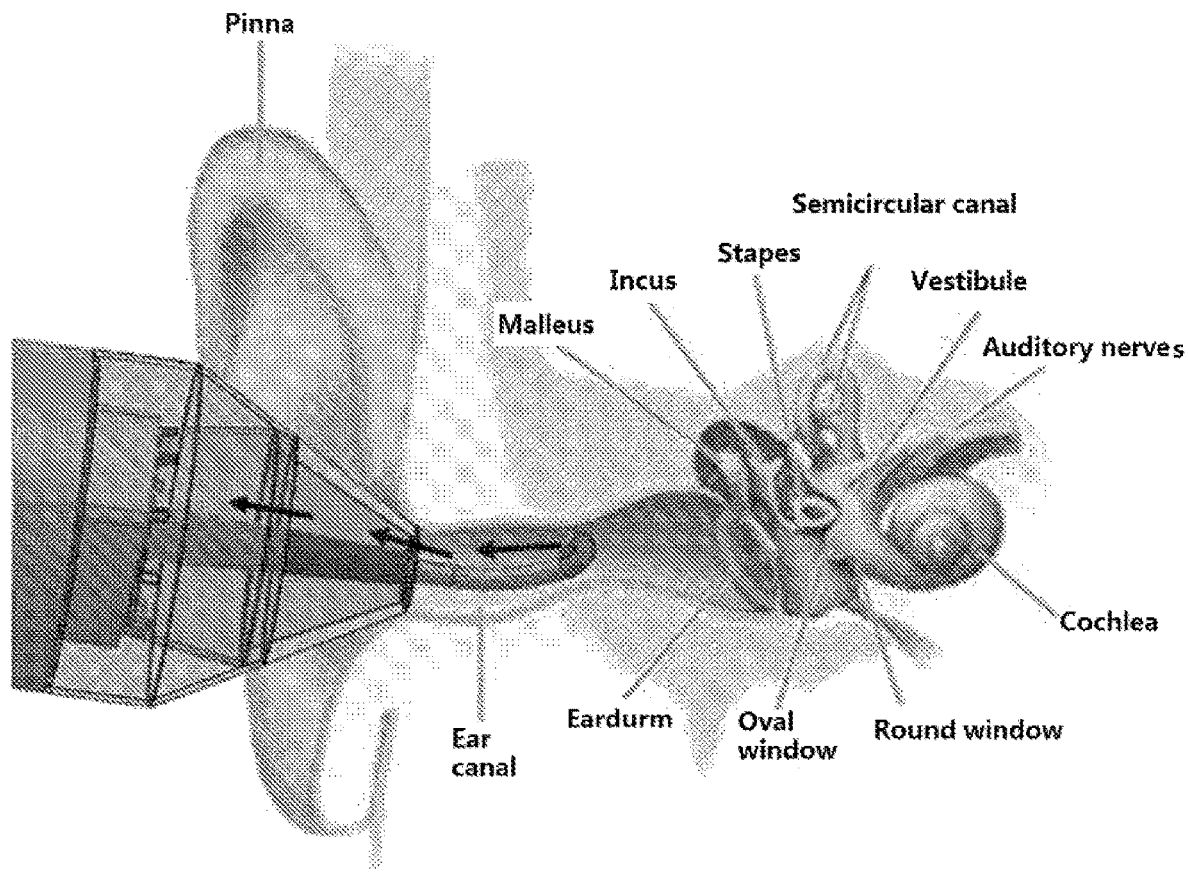
FIG. 6 is a use state view of the cerumen removing device according to an embodiment of the present application.

FIG. 6 is a use state view showing the use of the cerumen removing device according to an embodiment of the present application.

Referring to FIG. 6, the head section 200 may be configured to be curved toward the ear canal wall surface so that at least part of the head section 200 is in contact with the ear canal wall surface.

More specifically, the scrub head 210 of the head section 200 may be provided such that the flow path member 203 is bent toward the ear canal wall surface side so as to contact the ear canal wall surface.

The air ejection hole 201 is formed so that the discharged air flows toward the recovery hole 111. When the recovery hole 111 is in contact with the ear of the user, the air discharged out of the air ejection hole 201 flows on the inner wall surface of the ear canal of the user and sequentially passes through the recovery hole 111 and the discharge hole 121.

More specifically, the air discharged from the air ejection hole 201 passes through the recovery hole 111 together with the user's cerumen, and then both of the discharged air and the cerumen are introduced into the opening 122 of the cerumen storage member connected to the mounting hole 112, and the cerumen is stored in the cerumen storage member 120, while the air is discharged through the discharge hole 121 to the outside.

In particular, the air ejection hole 201 forms an angle of 45° to 90° with an assumed central axis G using the central axis G as a base line.

As described above, by forming the air ejection hole 201 in the particular way, the air discharged through the air ejection hole 201 can flow toward the recovery hole 111.

Therefore, the cerumen attached to the wall surface of the ear canal is pushed out in a direction towards the outside of the ear hole (towards the side of the recovery hole) by the pressure of the air discharged through the air ejection hole 201, so that the cerumen can be removed.

At this time, the air pressure produced is about 7 kPa to 14 kPa, or 9 kPa to 11 kPa, or below 10 kPa, but is not limited thereto.

As described above, the problem of directly applying pressure to the eardrum can be fundamentally prevented by discharging air towards the outside of the ear hole (towards the recovery hole), and the discomfort felt by the user due to the air pressure applied to the eardrum can be prevented.

In addition, as described above, by discharging the air, it is possible to remove and evaporate moisture, which is introduced into the ear of the user during face washing or bathing, to the outside of the ear.

On the one hand, the head section 200 can be disposed to be exposed to the outside through the recovery hole 111, and disposed in the container section 100 by going through the contact member 110 and the first connection member 120.

In particular, the sectional area of the recovery hole 111 may be formed to be larger than the sectional area of the head section 200, and the head section 200 is arranged to have a predetermined interval from the edge of the recovery hole 111 so as to form a predetermined area, and the cerumen can flow into the cerumen storage member 120 via the recovery hole 111 through the predetermined area.

The pump 300 may be disposed in the body section 100, and part of the pump may be disposed in the container section 100.

Moreover, the head section 200 can be made of a soft or hard material.

In particular, the scrub head 210 and the flow path member 203 can be made of a soft or hard material.

The soft or hard materials may have a Shore hardness of A30 to 90.

More specifically, the head section 200 may be made of a soft or hard material having a Shore hardness of A30 to 90 in order to control the contact force applied to the inner wall, that is the skin surface, of the ear canal at a prescribed magnitude.

In particular, a flow path member 203 curved toward the wall surface of the ear canal is made of a soft or hard material having elastic restoring force, so that, when the scrub head 210 connected to the flow path member 203 contacts the wall surface of the ear canal, according to the size of the user's ear canal, the flow path member 320 is unfolded, meanwhile, elastic energy can be accumulated by the bending stiffness of the flow path member 203.

This elastic energy can be applied to the ear canal wall surface in the form of an elastic contact force exerted by the scrub head 210 that is in contact with the ear canal wall surface.

That is, the flow path member 203 of the present application is made of a soft or hard material having a specified stiffness and a Shore hardness of A30 to 90, and is formed to bend toward the wall surface side of the ear canal with a predetermined angle, so that the scrub head 210 can easily contact the wall surface of the ear canal, and the elastic contact force applied to the wall surface of the ear canal can be restricted to be no more than a predetermined value even when the flow path member 203 is fully unfolded by the force applied by the user.

Therefore, when the flow path member 203 is fully unfolded due to the force applied by the user and the contact with the wall surface of the ear canal, the elastic contact force applied to the wall surface of the ear canal becomes a maximum value, and since the maximum value of the elastic contact force is restricted to be no more than a predetermined value, the physical irritation due to scrubbing of the ear canal wall is minimized.

For example, the soft or hard materials may be silicone rubber, thermoplastic rubber (TPR), polyvinyl chloride (PVC), and polyurethane (PU), but are not limited thereto.

In one aspect, the cerumen removing device 10 of the present application may comprise a motor 500 for rotating the head section 100.

For example, the motor 500 may be a stepping motor (stepping type motor).

More specifically, one side of the head section 200 is connected to the motor 500, and the head section 200 can be rotated by the rotational force transmitted from the motor 500.

In other words, the head section 200 can rotate in a circumferential direction of the wall surface of the ear canal, while being in contact with the wall surface of the ear canal.

Wherein, the head section 200 can be rotated 360 degrees in a circumferential direction of the wall surface of the ear canal, and the cerumen of the entire internal wall surface of the ear canal can be removed by the scrub head 210.

In particular, the head section 200 may be set to rotate in a forward or reversed direction by the motor 500 at a predetermined basic angle interval.

As described above, each predetermined basic angle interval is set as one step, and forward and reversed rotation can be repeated several times within one step of rotation.

In other words, when the head section 200 rotates in a forward rotation direction, forward and reversed rotation can be repeated several times in one step of rotation to complete a 360-degree forward circular rotation. Conversely, when rotating in a reversed rotation direction, forward and reverse rotation can be repeated several times in one step of rotation to complete a 360-degree reversed circular rotation.

For example, when the basic angle interval is set to 5° (degrees), a rotation of 5° (degrees) is set to be 1 step, and 360° (degrees) can be divided into 72 steps for rotation. The forward and reversed rotation can be repeated several times in each of the respective steps of rotation.

In other words, the inner circumference of the ear canal is divided into 72 unit sectors, and forward and reversed rotation are repeated within a unit sector having a sector angle of 5° (degrees). In particular, the rotation and reversed rotation can be repeated for about 5 times, but is not limited thereto.

As described above, the forward and reversed rotation are performed repeatedly to complete a forward circular rotation over the 72 unit sectors, and the forward and reversed rotation are performed repeatedly for about 5 times over each of the 72 unit sectors to complete a reversed circular rotation.

As described above, the scrub head 210 scrubs the wall surface of the ear canal by the forward and reversed rotation over 360 degrees along the circumferential direction of the ear canal wall surface, thereby reducing the adhesion of oily cerumen and the interlocking of dry cerumen, which are tightly attached to the internal wall surface of the ear canal.

Meanwhile, air is discharged to the wall surface of the ear canal through the air ejection hole 201, which makes it much easier to remove cerumen.

In the present application, when air pressure is applied through the air ejection hole 201 to remove the cerumen attached to the wall surface of the ear canal, the physical stimulus applied to the skin surface of the ear canal can be minimized when removing the cerumen.

However, when the cerumen is tightly attached to the skin surface of the ear canal, it may be difficult to completely remove cerumen only by air pressure. Therefore, cerumen can be more easily removed by finely scrubbing the entire inner wall area of the ear canal with the scrub head 210 and at the same time applying air pressure through the air ejection hole 201.

The dry cerumen has a characteristic of being fragile under mechanical pressure, so it can be easily detached from the surface of the ear canal only by the scrubbing action, and can be easily discharged to the container section 100 by the air ejection pressure.

The oily cerumen is internally dried by the air ejected from the air ejection hole 201 of the present application, and thus a surface tension is generated along the boundary line of the cerumen in contact with the skin, so that the cerumen can also be easily detached from the skin.

Therefore, the oily cerumen can be easily separated from the skin by the ejected air, and at the same time, it becomes similar in nature to the dry cerumen by means of the drying process, such that it will be easily fragmented by a scrubbing operation.

In other words, according to the present application, the head section 200 performs the scrubbing operation and the air ejection at the same time, so that the removal efficiency of both the dry cerumen and the oily cerumen can be improved.

In addition, as described above, the cerumen is detached from the skin surface of the ear canal, discharged out of the ear canal and captured in the container part 100 through the scrubbing operation of the head section 200 with a minimum physical force based on the restricted contact force.

Furthermore, the cerumen removing device 10 of the present application may further comprise a moisture supply device (not shown) provided to spray a small amount of moisture to the wall surface of the ear canal to supply moisture thereto.

As described above, when the moisture is supplied by the moisture supply device, the interlocking of the dry cerumen can be weakened by the supplied moisture, so that the pain incurred when removing the cerumen is reduced, and the scrubbing effect of the scrub head 210 can be improved.

Wherein, the moisture may include physiological saline, water, and the like, but is not limited thereto.

The motor 500 may be arranged in the body section 400 and disposed adjacent to the pump 300.

In particular, the motor 500 may comprise a connector 510 for connecting the pump 300 and the motor 500.

For example, a first joint portion connected to at least part of the pump 300 is disposed at one side of the connector 510, and a second joint portion connected to at least part of the motor 500 is disposed at the other side of the connector 510.

In one aspect, the cerumen removing device 10 of the present application may comprise a driving part 600 for moving the head section 200 forward or backward.

The driving part 600 may comprise a linear guide.

The linear guide is an electric transmission device, and can be set to drive forward or backward at a predetermined speed when the driving part is actuated.

Wherein, the forward or backward movement can be repeated.

The driving part 600 is connected to the head section 200, and can be configured to slide the head section 200 toward the inside of the ear canal of the user at a predetermined speed.

More specifically, the driving part 600 can be connected to one side of the motor 500.

In other words, the motor 500 can be moved at a predetermined speed by the driving of the driving part 600.

As described above, the head section 200 of the present application is connected to the pump 300, and the pump 300 is connected to the motor 500 through the connector 510, and the motor 500 is connected to the driving part 600, so that the motor 500, the pump 300, and the head section 200 can be driven to move slidably forward or backward by the driving part 600.

The motor 500, the pump 300, and the head section 200 are integrally arranged through the connector 510, and can be moved forward or backward simultaneously at a predetermined speed by the driving part, which is a linear guide.

In particular, the rotational force transmitted from the motor 500 rotates the pump 300 through the connector 510, such that the head section 200 connected to the pump 300 can be rotated.

Therefore, the head section 200 can be moved toward the inside of the ear canal of the user by the driving part 600, and at this time, the head section 200 can move to a depth of 15 to 20 mm inside the ear canal.

As described above, the head section 200 steadily enters the inside of the ear canal of the user at a predetermined speed, and the scrubbing operation can be continuously performed from the entrance of the ear hole to a predetermined depth inside the ear canal for continuously removing the cerumen.

In particular, by restricting the entry depth of the head section 200 in a range of 15 to 20 mm, only the cerumen that has been pushed out to the outer part of the ear canal is removed, and therefore the effect of maintaining the physiological circulation function of the cerumen formed at the inner part of the ear canal is maximized.

If the user is an elderly person or a disabled person, who has difficulty in adjusting the strength and movement delicately, or a user who is sensitive to skin irritation, the head section 200 would produce great pain when it moves rapidly in a state of being in contact with the skin. Therefore, the speed of the head section automatically moving forward or backward inside the ear canal is reduced and stably adjusted by the driving part, so that the user does not feel a big discomfort, and the cerumen of the user can be removed automatically.

Figure 7:
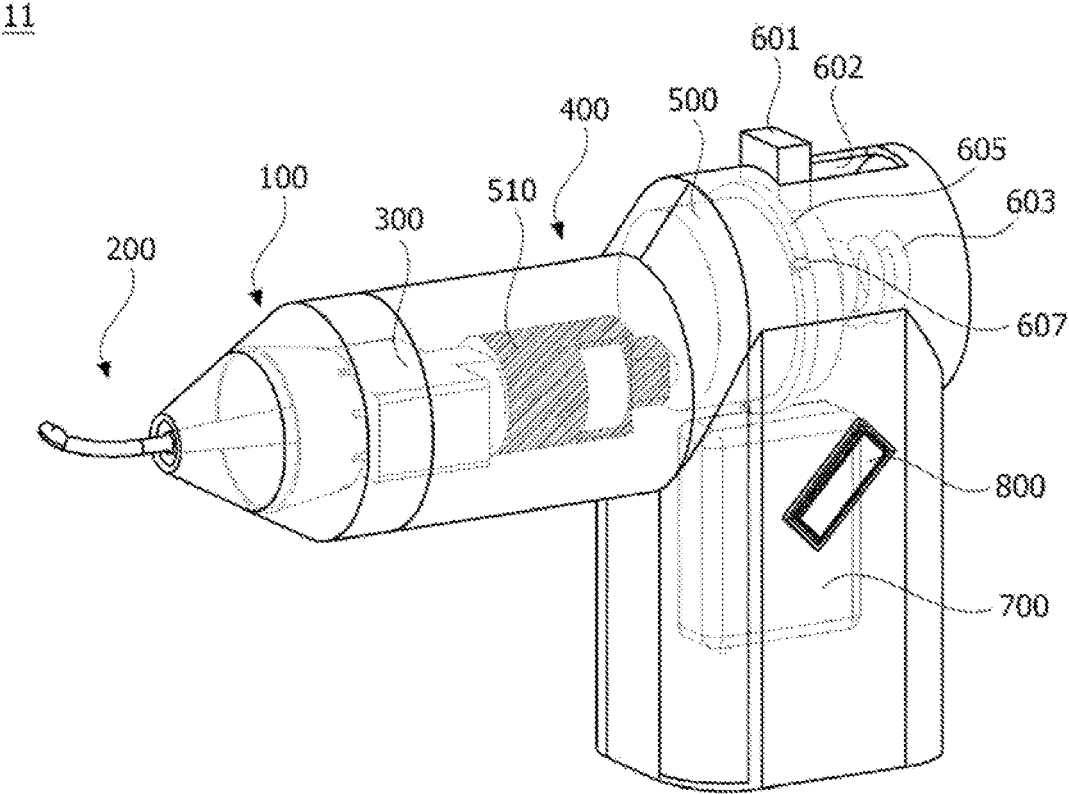
FIG. 7 is an internal perspective view of a cerumen removing device according to another embodiment of the present application.
Figure 8:
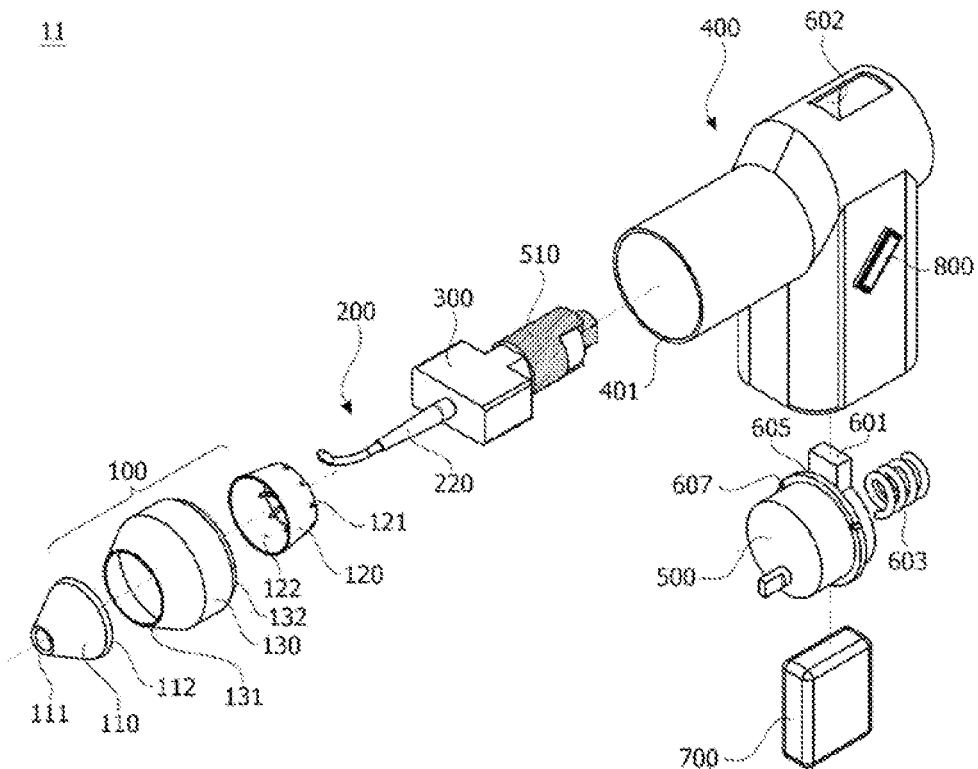
FIG. 8 is an exploded perspective view of a cerumen removing device according to another embodiment of the present application.

In another aspect, FIG. 7 and FIG. 8 are an internal perspective view and an exploded perspective view showing a cerumen removing device 11 according to another embodiment of the present application. For the convenience of description, the same reference numerals are used for the parts similar to the previous embodiments, and the descriptions of the parts that common to the previous embodiments are omitted.

More specifically, referring to FIG. 7 and FIG. 8, the driving part 600 of the cerumen removing device 11 according to another embodiment of the present application is different from the previous embodiments and can be manually adjusted.

The driving part 600 may comprise an operation part 601 which is connected to the head section 200 to drive the head section to move forward or backward, and the operation part 601 is exposed to the outside.

More specifically, the driving part 600 may comprise an operation part 601, a return spring 603, and a slip ring 605.

For example, the operation part 601 may be protruding on one side of the motor 500.

In addition, an operation hole 602 for exposing the operation part 601 to the outside can be formed at one side of the body section 400.

In other words, the motor 500 is disposed in the body section 400, and the operation part 601 protruding from the motor 500 is exposed to the outside of the body section 400 through the operation hole 602.

The operation hole 602 is formed to have a predetermined length, and is able to guide the operation portion 601 to move forward or backward.

In other words, the operation part 601 can be configured to move forward or backward along the length direction of the operation hole 602.

When the user moves the operation part 601 along the length direction of the operation hole 602 with a finger, the head section 200 connected to the operation part 601 can move forward or backward inside the ear canal.

In other words, as described above, the head section 200 of the present application is connected to the pump 300, and the pump 300 is connected to the motor 500 through the connector 510, and the motor 500 is connected to the operation part 601, therefore, as the user moves the operation part 601, the motor 500, the pump 300 and the head section 200 can be moved forward or backward.

The motor 500, the pump 300 and the head section 200 are integrated by the connector 510, and can be moved forward or backward simultaneously by manual operation of the operation part 601.

In particular, the operation part 601 further comprises a slip ring 605 for easier movement of the operation part 601.

The slip ring 605 may comprise a plurality of rollers 607 that are in contact with an inner peripheral surface of the body section 400 and are provided to be movable along the inner peripheral surface.

The rollers 607 may be arranged at predetermined intervals along the circumferential direction of the slip ring 605.

In addition, the slip ring 605 is arranged on the outer circumference of the motor 500. When the operation part 601 is moved, the plurality of rollers 607 of the slip ring rotate and move along the inner peripheral surface of the body section 400, so that the user can more easily move the operation part 601.

In addition, the return spring 603 can be configured to automatically reset the head section 200 when the user releases the finger after operating the operation part 601 to advance the head section 200.

For example, the return spring 603 is connected to an inner surface of the body section 400 and connected to the motor 500, such that when a force is not applied to the operation part 601, the motor 500 connected to the return spring 603 is moved toward the inside of the body portion 400 (backward direction) by the return spring 603.

Therefore, ordinary users who are not sensitive to skin irritation can adjust the forward or backward movements at a desired speed, so that the head section 200 can be moved immediately, realizing the effect that the depth and insertion times of the head section 200 being inserted into the ear canal can be arbitrarily adjusted.

On the one hand, in the present application, the linear guide, the operation part 601, the return spring 603 and the slip ring 605 can be appropriately adapted so that they can be used according to a selection of a manual mode or an automatic mode by the user.

Wherein, the body section 400 may further comprise a mode selection portion (not shown) configured to allow a user to select a manual or automatic mode.

When the user selects the automatic mode, the linear guide is driven to slide the head section toward the inside of the ear canal of the user at a predetermined speed, and the head section enters the inside of the ear canal at a predetermined speed to remove the cerumen from the wall surface of the ear canal by scrubbing and discharged air pressure.

When the user selects the manual mode, the user directly operates the operation part 601 with his hand to slide the head section to the inside of the ear canal, thereby removing the cerumen from the wall surface of the ear canal.

On the one hand, a battery 700 can be disposed inside the body section 400, and the battery 700 is electrically connected to the pump 300, the motor 500, and the driving part 600 for supplying power thereto.

Furthermore, the cerumen removing device 10 or 11 of the present application may comprise a user identification section 800 configured to be capable of storing and identifying device usage information of a user.

The user identification section 800 may be a fingerprint identification device (fingerprint identification sensor), and can be disposed on an outer surface of the body section 400.

More specifically, the user identification section 800 is disposed at a position where the user's thumb touches the device when the user holds the device 10 or 11. Various information about the user, such as the number of times the device is used by the user and at what time the device is used by the user, is stored in the device by setting a pre-logged user, or setting automatic logging by the user during use, etc.

In addition, the stored user information can be stored on an online network through a wireless transmission device such as WIFI (Near Field Wireless Local Area Network).

In particular, users can confirm their own usage information stored on the Internet using an application on a smartphone. The application can be set to analyze the user's information and provide appropriate warning or suggestion in voice and text forms.

In addition, the warning or suggestion can be provided to the user in voice form by using a separate storage device, information analysis software and a built-in speaker.

As mentioned above, the method of warning and suggesting to users is associated with the users with frequent cerumen impaction and a management program for the purpose of preventing cerumen impaction. For users with frequent cerumen impaction, a reminder module can be added to the device based on the user's device usage information, and the reminder module has a reminding function for periodically supervising and encouraging the use of the device.

In other words, the user identification section 800 of the present application may be configured to provide appropriate reminder and suggestion to the user in voice information and text forms through applications in the smart phone and a plurality of devices provided in the cerumen removing device 10 or 11.

Further, a switch (not shown) for activating the device 10 or 11 is disposed on an outer surface of the body section 400, and the device 10 or 11 can be driven by turning on or turning off the switch.

In addition, a mode selection portion (not shown) for selecting an automatic mode or a manual mode of the device 10 or 11 may be disposed on an outer surface of the body section 400.

In particular, according to the mode selection, the driving part 600 can be driven in an automatic mode, or the user can operate to drive the operation part 601 in a manual mode.

For example, in the above-mentioned cerumen removing device 10 or 11 of the present application, an operation part 601 may be provided on an upper portion of the motor 500, and a linear guide may be connected to a lower portion of the motor. A pump 300 can be connected to a front side (a side near the container section) of the motor, and a return spring can be connected to the rear side of the motor.

Therefore, if the driving part 600 is driven, the motor 500 connected to the driving part 600 advances, the pump 300 connected to the motor 500 advances inside the device, and the head section 200 connected to the pump advances to the outside through the recovery hole 111 and thus can be inserted into the ear canal.

At this time, when the user operates through the operation part 601, the motor connected to the operation part 601 advances, the pump 300 connected to the motor 500 advances inside the device, and the head section 200 connected to the pump advances to the outside through the recovery hole 111 and thus can be inserted into the ear canal. When the force applied to the operation part 601 is released, the head section 200 moves back to the inside of the device by the return spring 603 and thus can be reset.

Figure 9:
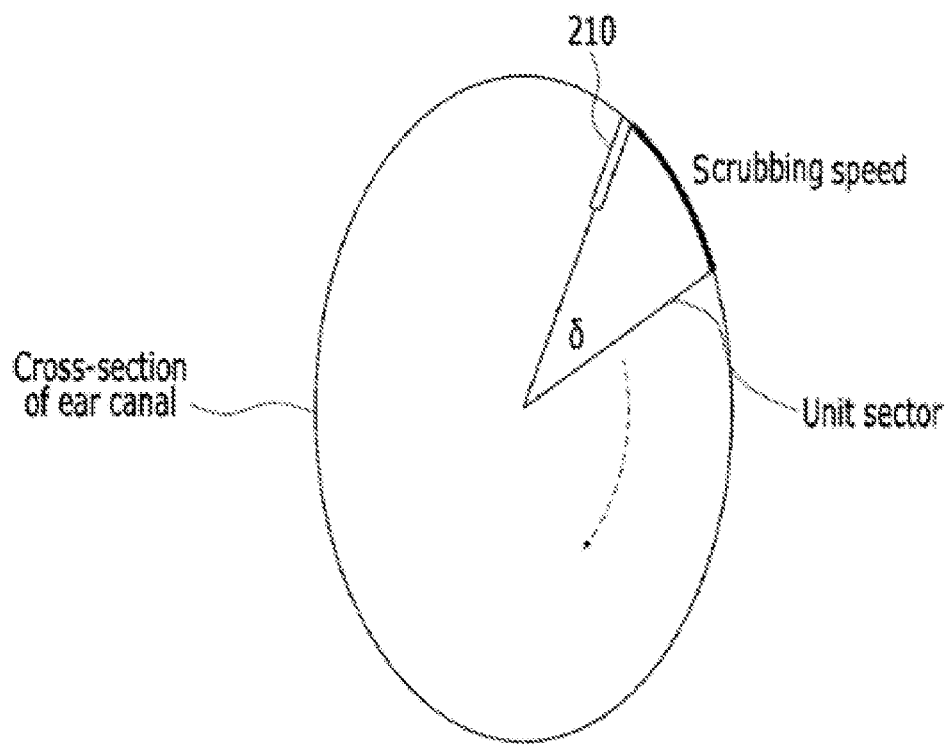
FIG. 9 is a schematic view showing the operation of a cerumen removing device according to an embodiment of the present application.

FIG. 9 is a schematic view showing the operation of a cerumen removing device according to an embodiment of the present application.

Referring to FIG. 9, the operation of the cerumen removing device according to an embodiment of the present application can be substantially controlled by two parameters.

The first parameter is the angle of the unit sector, and the second parameter is the scrubbing speed of the scrub head 210 for scrubbing the wall surface of the ear canal according to the angle of the unit sector.

More specifically, the unit sector angle of the cerumen removing device according to an embodiment of the present application may be 5° to 20°.

If the angle of the unit sector is less than 5°, the time required to scrub the wall surface of the ear canal increases, which leads to a problem that it is difficult for a user to remove cerumen efficiently.

If the angle of the unit sector is 20°, the frictional force acting on the wall surface of the ear canal increases, and there is a problem that an unexpected skin irritation will occur on the wall surface of the ear canal of the user.

In one aspect, the scrubbing speed may be 5 mm/s to 50 mm/s.

If the scrubbing speed is less than 5 mm/s, the time required to scrub the wall surface of the ear canal increases, which leads to a problem that it is difficult for a user to remove cerumen efficiently.

If the scrubbing speed unit sector is higher than 50 mm/s, the frictional force acting on the wall surface of the ear canal increases, which leads to a problem that an unexpected skin irritation will occur on the wall surface of the ear canal of the user.

However, the above description is only an example for the convenience of description, and the physical conditions of the scrub head 210 that satisfy both of these parameters need to be considered together. The scrub head 210 can be modified in various ways according to the needs of the user, which does not limit the protection scope of the present application.

Figure 10:
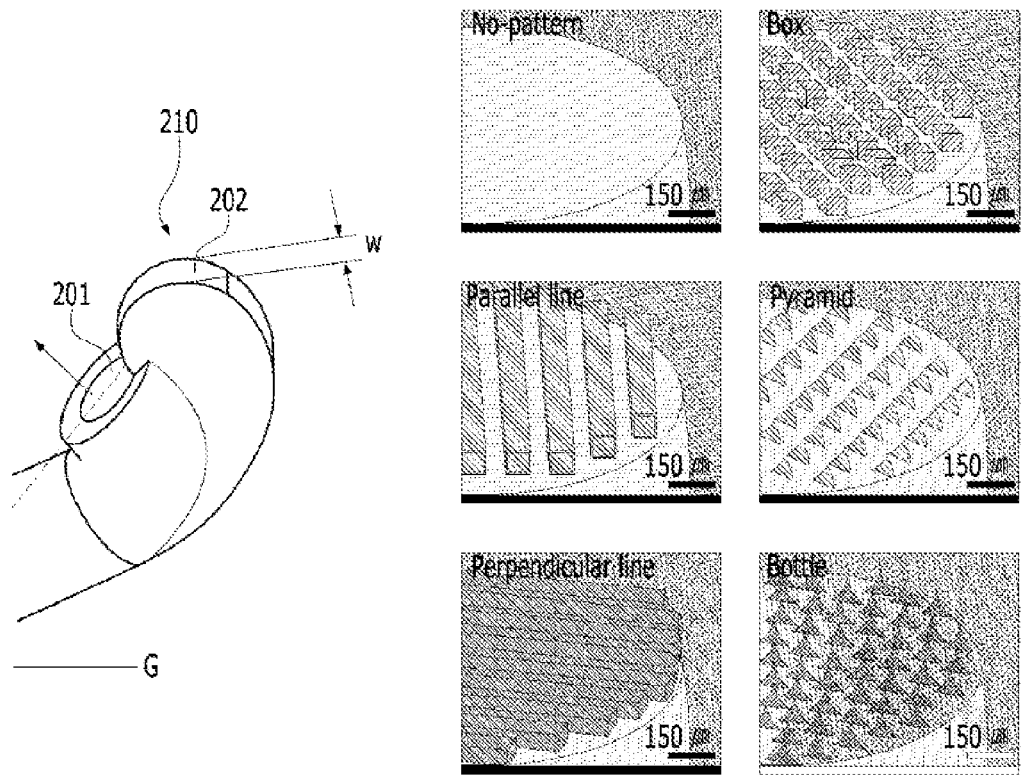
FIG. 10 is a view showing a head section according to another embodiment of the present application.

FIG. 10 is a view showing a head section according to another embodiment of the present application.

Referring to FIG. 10, a circular contact surface 202 of the head section 210 according to another embodiment of the present application is provided with various micro-patterns, and the circular contact surface 202 may have a first width W.

The first width W may be 0.5 mm to 2 mm.

When the first width W is less than 0.5 mm, as described above, the space on the circular contact surface 202 for arranging the plurality of micropatterns is reduced, which leads to a problem that the effect of the micro-pattern for efficiently removing cerumen may be decreased.

Conversely, when the first width W is greater than 2 mm, the contact pressure applied by the circular contact surface 202 to the wall surface of the ear canal decreases, which may lead to a problem that the cerumen cannot be efficiently removed.

Therefore, the width of the circular contact surface 202, i.e., the first width W, of the present application is 0.5 mm to 2 mm, which has the effect that the user can remove the cerumen more efficiently.

On the one hand, the circular contact surface 202 may be provided with various micro-patterns. As shown in FIG. 10, the circular contact surface may be provided with no-pattern, a box-pattern, a parallel line-pattern, a pyramid-pattern, a perpendicular line-pattern, a bottle-pattern and many other patterns.

In this way, the circular contact surface 202 is provided with a variety of micro-patterns. Even if the two parameters described above, i.e., the unit sector and the scrubbing speed, are defined as constant, a skin irritation on the wall surface of the ear canal of the user can be prevented and a rubbing friction can be provided to remove the cerumen more efficiently.

For example, the inventors have confirmed that when a parallel line-pattern is formed on the circular contact surface 202, a friction coefficient of 1 or more is generated under a load of 2 mN, and a mucous membrane layer tends to fall off under a contact force of 10 mN.

As described above, various micro-patterns formed on the circular contact surface 202 can be formed by using various UV-curable polymer materials with a PDMS mold, and can also be formed by electrical discharge machining (EDM) According to the needs of users, micro-patterns can be formed on the circular contact surface 202 in various ways, which does not limit the protection scope of the present application.

INDUSTRIAL APPLICABILITY

The application relates to an automatic cerumen removing device for automatic cerumen removal, which has industrial applicability in health management supermarket and pet management supermarket.

I claim:

1. A cerumen removing device, comprising:
   a container section comprising a recovery hole and a discharge hole;
   a head section exposed to the outside through the recovery hole and having at least one air ejection hole;
   a pump configured to discharge air to the outside through the air ejection hole; and
   a driving part for moving the head section forward or backward.

2. The cerumen removing device according to claim 1, wherein,
   the air ejection hole is formed to direct the discharged air towards the recovery hole, and when the recovery hole contacts an ear of an user, flowing of the air discharged by the air ejection hole on an inner wall of an ear canal of the user is enhanced and the air sequentially pass through the recovery hole and the discharge hole.

3. The cerumen removing device according to claim 2, wherein,
   the air ejection hole forms an angle of 45° to 90° with an assumed central axis using the central axis as a base line.

4. The cerumen removing device according to claim 1, wherein,
   the head section comprises a flow path member having a predetermined length and having an air passage connected to the air ejection hole.

5. The cerumen removing device according to claim 1, wherein,
   the head section is configured to be curved toward a wall surface of an ear canal so that at least part of the head section is in contact with the wall surface of the ear canal.

6. The cerumen removing device according to claim 1, wherein,
   the head section comprises a scrub head which has the air ejection hole and is in contact with a wall surface of an ear canal.

7. The cerumen removing device according to claim 1, comprising a motor for rotating the head section.

8. The cerumen removing device according to claim 7, wherein, the motor is a stepping motor.

9. The cerumen removing device according to claim 1, wherein,
   the driving part comprises a linear guide.

10. The cerumen removing device according to claim 1, comprising an operation part which is connected to the head section and exposed to the outside for moving the head section forward or backward.

11. The cerumen removing device according to claim 1, comprising a user identification section configured to store and identify device usage information of a user.

12. The cerumen removing device according to claim 1, wherein,
    the head section is configured to move with a unit sector angle of 5° to 20° on a wall surface of an ear canal.

13. The cerumen removing device according to claim 1, wherein,
    the head section is configured to scrub a wall surface of an ear canal at a scrubbing speed of 5 mm/s to 50 mm/s.

14. The cerumen removing device according to claim 1, wherein,
  a circular contact surface disposed on the head section for scrubbing a wall surface of an ear canal has a width of 0.5 mm to 2 mm.

15. The cerumen removing device according to claim 1, wherein,
  a circular contact surface disposed on the head section for scrubbing a wall surface of an ear canal is provided with a micro-pattern.

* * * * *

UNITED STATES PATENT AND TRADEMARK OFFICE
CERTIFICATE OF CORRECTION

PATENT NO. : 11,324,636 B2  
APPLICATION NO. : 16/739185  
DATED : May 10, 2022  
INVENTOR(S) : Young-Tae Kim Page 1 of 1

It is certified that error appears in the above-identified patent and that said Letters Patent is hereby corrected as shown below:

On the Title Page

At item (71) please replace Applicant: OROLOGYLAB HEALTHCARE INC., Gyeonggi - Do ( KR )
with Applicant: OROGYLAB HEALTHCARE INC., SEOUL, KOREA, REPUBLIC OF At item (73) please replace Assignee: OROLOGYLAB HEALTHCARE INC., Gyeonggi - Do ( KR )
with Assignee: OROGYLAB HEALTHCARE INC., SEOUL, KOREA, REPUBLIC OF Signed and Sealed this  
Twenty-eighth Day of March, 2023

Katherine Kelly Vidal  
*Director of the United States Patent and Trademark Office*